United States Patent
Brown

(10) Patent No.: US 7,775,999 B2
(45) Date of Patent: Aug. 17, 2010

(54) APPARATUS AND METHOD FOR USE OF A HIP BRACE

(76) Inventor: Randall Brown, 6276 Grangers Dairy Dr., Sacramento, CA (US) 95818

(*) Notice: Subject to any disclaimer, the term of this patent is extended or adjusted under 35 U.S.C. 154(b) by 627 days.

(21) Appl. No.: 10/956,454

(22) Filed: Oct. 1, 2004

(65) Prior Publication Data
US 2006/0074365 A1 Apr. 6, 2006

(51) Int. Cl.
*A61F 5/37* (2006.01)
*A61F 13/00* (2006.01)
*A63B 57/00* (2006.01)
*A63B 53/06* (2006.01)
*A63B 53/16* (2006.01)

(52) U.S. Cl. .............. 602/24; 602/5; 602/23; 602/25; 128/846; 128/869; 128/882; 473/215; 473/277

(58) Field of Classification Search .......... 602/4, 602/19, 23–25, 60–62, 75; 128/845, 869, 128/882; 473/215, 277
See application file for complete search history.

(56) References Cited

U.S. PATENT DOCUMENTS

| | | | | |
|---|---|---|---|---|
| 976,564 A | * | 11/1910 | Goodson | 128/845 |
| 4,524,760 A | * | 6/1985 | Lerner | 128/845 |
| 4,593,697 A | * | 6/1986 | Salort | 450/144 |
| 4,709,692 A | * | 12/1987 | Kirschenberg et al. | 602/19 |
| 4,901,710 A | * | 2/1990 | Meyer | 602/24 |
| 4,977,893 A | * | 12/1990 | Hunt | 602/61 |
| 5,286,251 A | * | 2/1994 | Thompson et al. | 602/23 |
| 5,423,852 A | * | 6/1995 | Daneshvar | 606/201 |
| 5,425,702 A | * | 6/1995 | Carn et al. | 602/62 |
| 5,445,114 A | * | 8/1995 | Walker | 119/857 |
| 5,486,194 A | * | 1/1996 | Kawasaki et al. | 606/203 |
| 5,814,001 A | * | 9/1998 | Schwenn et al. | 602/24 |
| 5,928,175 A | * | 7/1999 | Tanaka | 602/75 |
| 6,210,353 B1 | * | 4/2001 | Barnes | 602/19 |
| 6,428,495 B1 | * | 8/2002 | Lynott | 602/23 |
| 6,652,596 B2 | * | 11/2003 | Smith et al. | 623/32 |
| 6,832,960 B2 | * | 12/2004 | Thony | 473/277 |
| 2002/0082537 A1 | * | 6/2002 | MacAllister | 602/4 |
| 2003/0009120 A1 | * | 1/2003 | MacAllister | 602/23 |
| 2004/0230150 A1 | * | 11/2004 | West | 602/19 |

FOREIGN PATENT DOCUMENTS

DE 3122462 * 12/1982

* cited by examiner

*Primary Examiner*—Patricia M Bianco
*Assistant Examiner*—Brandon Jackson
(74) *Attorney, Agent, or Firm*—John P. O'Banion

(57) ABSTRACT

A support apparatus comprising a waist band, a thigh band, a lateral vertical strap attached to said waist band and two extensions attached to said thigh band, and a medial vertical strap attached to said waist band then wrapping medially down around the thigh and attaching to the thigh band.

13 Claims, 6 Drawing Sheets

APPARATUS AND METHOD FOR USE OF A HIP BRACE

BACKGROUND

1. Field of the Invention

The present invention relates to apparatus for supporting a person's hip.

2. The Prior Art

Background

The present invention is designed to enhance biomechanical function. In particular the present invention is designed to alleviate pain associated with arthritis, labrum tears, loose bodies, post surgical hip replacement or arthroscopy, prophylactic support to help minimize worsening of pathologic conditions, following surgery, or to help prevent surgery. Also, it is designed to enhance biomechanical function and duration of strenuous activities such as athletics or physical labor. It also enhances mechanical stability of the lower lumbar spine and pelvis.

Other braces are rigid, using plastic and/or metal components and predominately are designed for limiting hip joint motion. The present embodiment brace is elastic, light weight, and provides for enhanced biomechanical function.

BRIEF DESCRIPTION OF THE DRAWING FIGURES

DETAILED DESCRIPTION

Figure 1:
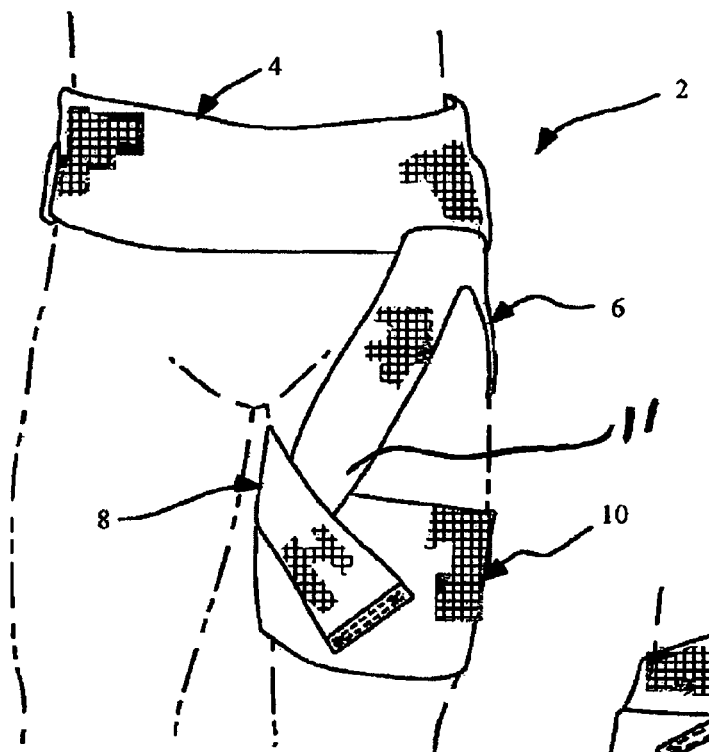
FIG. 1 is a front view of one embodiment of the hip brace as worn.

Persons of ordinary skill in the art will realize that the following description is illustrative only and not in any way limiting. Other modifications and improvements will readily suggest themselves to such skilled persons having the benefit of this disclosure. In the following description, like reference numerals refer to like elements throughout.

FIG. 1 is an anterior view of one embodiment of the hip brace 2 as worn. The hip brace 2 consists of a waist band 4, lateral vertical strap 6, medial vertical strap 8, and a thigh band 10. As seen in this view the lateral vertical strap 6 is secured to the waist band 4 proximate to the side of the hip and a first extension 11 is secured proximate the anterior aspect of the thigh band 10 between the lateral and medial aspect of the thigh band 10. The medial vertical strap 8 is secured to the posterior of the waist band 4 (not seen) then wraps down and around the leg and is secured to the thigh band 10 proximate the anterior aspect of said thigh band 10 between the lateral and medial aspect. In another embodiment, elastic bands may be added to the interior of the waist band to increase the elasticity of the waist band.

Figure 2:
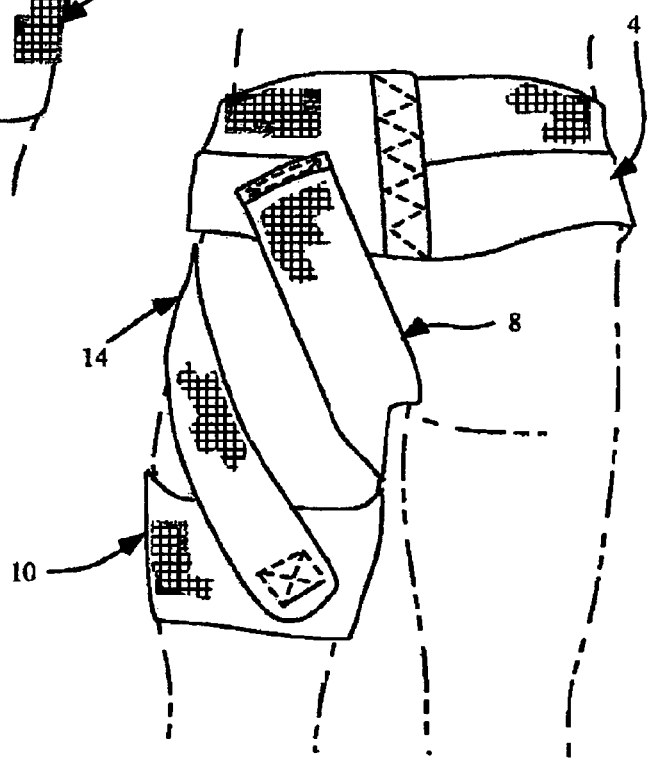
FIG. 2 is a posterior view of one embodiment of the hip brace as worn.

FIG. 2 is a posterior view of one embodiment of the hip brace 2 as worn. As seen in this view, the medial vertical strap 8 is attached to the waist band 4 at the posterior of the hip and wraps down and around the leg to the anterior aspect of said thigh band 10 between the lateral and medial aspect (not seen). The second extension 14 of the lateral vertical strap 6 wraps down and around the thigh and is attached to the posterior of the thigh band 10.

Figure 1A:
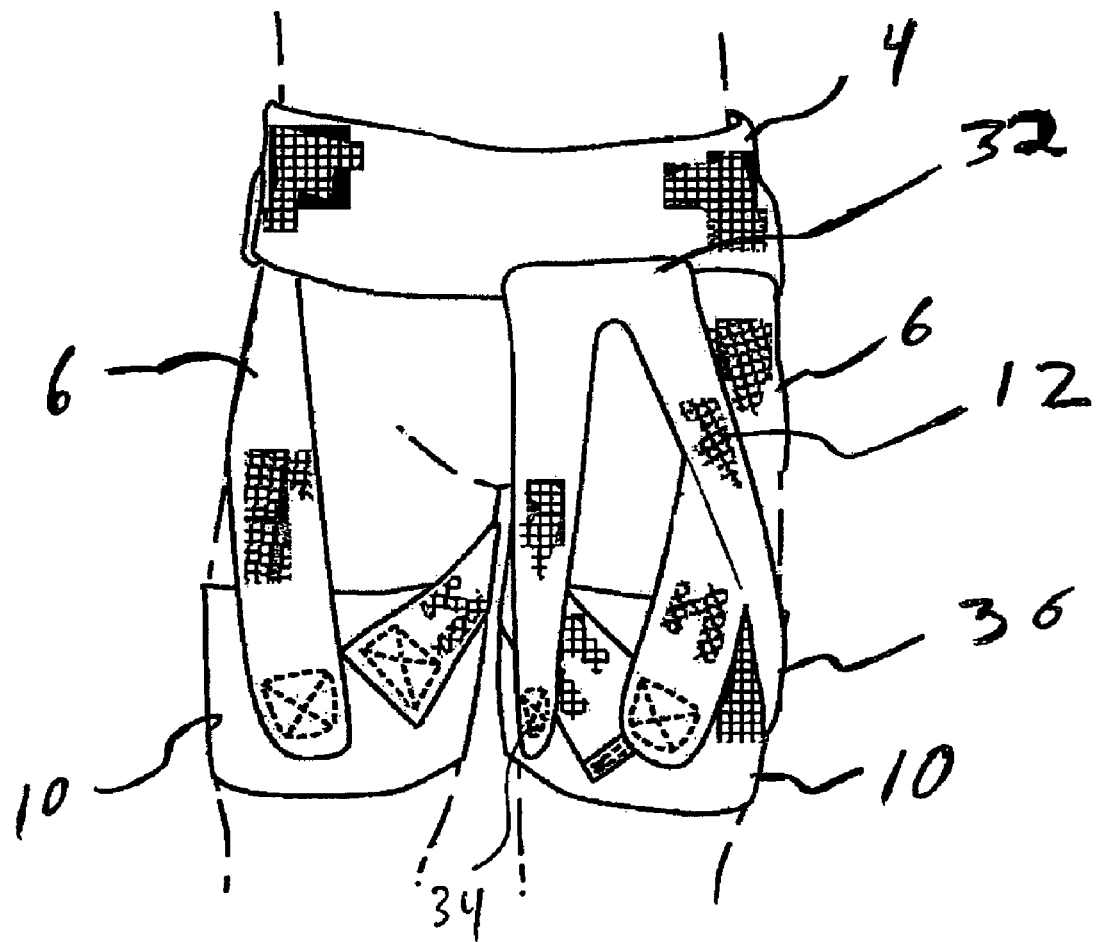
FIG. 1a is a front view of one embodiment of the hip brace as worn in a bilateral configuration with a utility strap.

FIG. 1a is a front view of one embodiment of the hip brace as worn in a bilateral configuration with lateral strap 6 and utility strap 12. The lateral strap 6 is attached as discussed above. The utility band 12 has a first end 15, a second end 51 and a midpoint 53. The first end 34 is removeably attached to the thigh band 10 proximate the anterior aspect of the thigh band 10 proximate the medial aspect of the thigh band 10. The midpoint 32 is removeably attached to the waist band 4 proximate the front of the person's hip. The second end 36 is removeably attached to the thigh band 10 proximate the anterior aspect of the thigh band 10 proximate the lateral aspect of thigh band 10.

Figure 3:
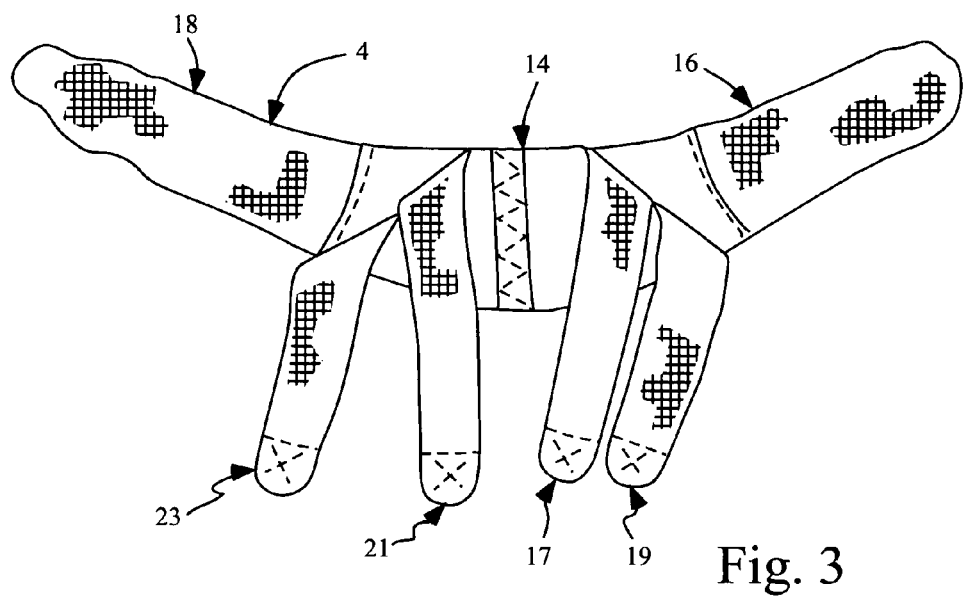
FIG. 3 is a view of the waist band 4.

FIG. 3 is a view of the waist band 4. The waist band 4 consists of a first layer 14, which includes a right flap 16 and a left flap 18. The right and left flap 16, 18 are attached to the first layer 14. The waist band 4 is manufactured from an elastic material such as neoprene. Further, the interior surface is smooth. The exterior surface of the right and left flap consists of a hook and loop system for attaching lateral vertical strap, medial vertical strap and a utility strap. The first layer 14 is wrapped tightly around the user's waist and may be secured at the right flap 16 and a left flap 18 by use of a hook and loop system, a buckle or a combination of the two. In the present embodiment, the right and left flap 16, 18 are sewn to the first layer 14 proximate a midpoint of the waist band 4. The right and left flap 16, 18 are used for securing the lateral vertical strap 6 and a utility strap 12. The right flap 16 is secured to the left flap 18 by use of a hook and loop system, a buckle or a combination of the two. In another embodiment, the right and left flaps 16, 18 may be secured to the first layer and/or each other using a hook and loop system. In a further embodiment, the second layer may consist of right flaps 17, 19 and left flaps 21, 23 may consist of a plurality of flaps or single flaps to which are secured to each other as described above.

Figure 4:
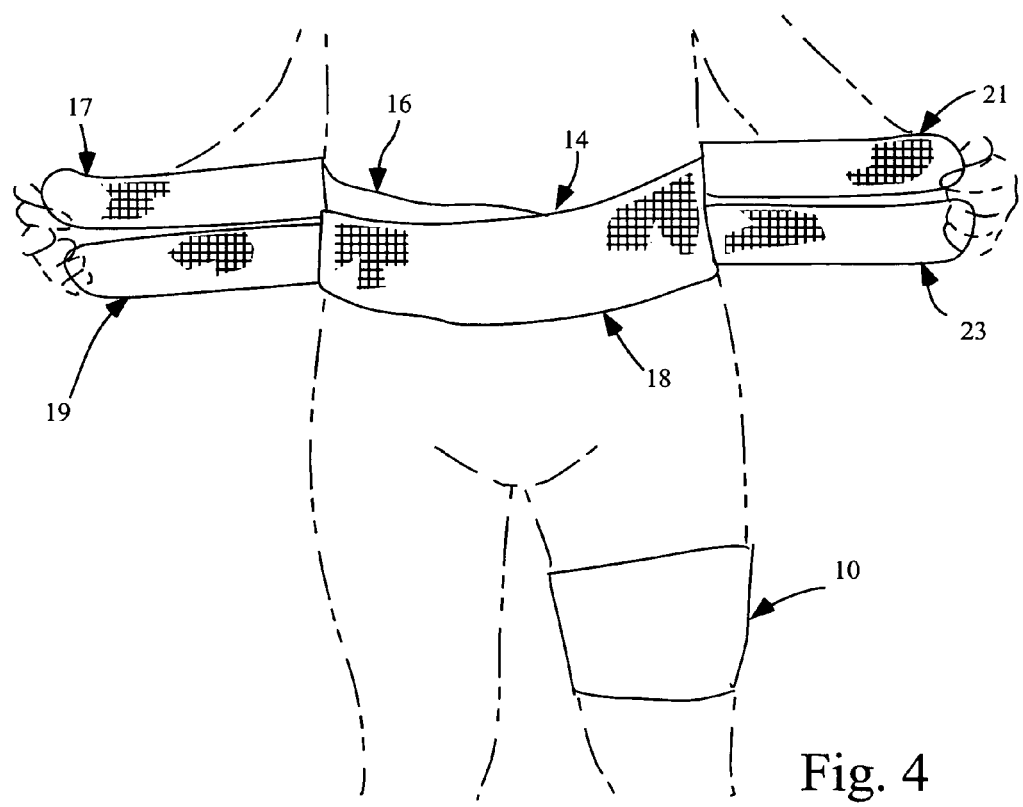
FIG. 4 is a person installing the waist band.

FIG. 4 is a person installing the waist band 4. In this instance, the person has wrapped the first layer of the waist band 4 around the waist. In the present embodiment, the waist band 4 is being held in place by a hook and loop system. The right and left flap 16, 18 are secured to the persons waist. The second layer may consist of either a single flap on either side or a dual flap system as shown. The right dual flaps 17, 19 and the left dual flaps 21, 23 are being held by the person.

Figure 5A:
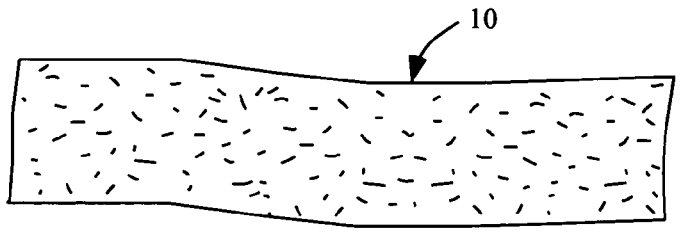
FIG. 5a is a drawing of one side of the thigh band.
Figure 5B:
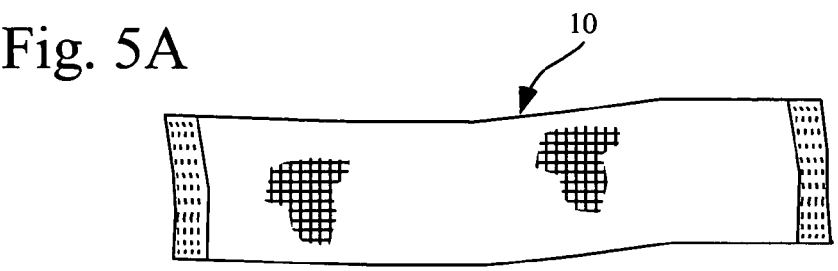
FIG. 5b is a drawing of the other side of the thigh band.

FIG. 5a is a drawing of one side of the thigh band 10. The thigh band 10 is wrapped around a person's thigh just above the knee and secured by a system of hooks and loops, a buckle or a combination of the two. In the present embodiment the thigh band 10 is manufactured from an elastic material such as neoprene. Further, the interior surface is smooth. The exterior surface consists of a hook and loop system for attaching lateral vertical strap, medial vertical strap and a utility strap. FIG. 5b is a drawing of the other side of the thigh band 10. In another embodiment, the thigh band 10 may be contoured for a better fit.

Figure 6:
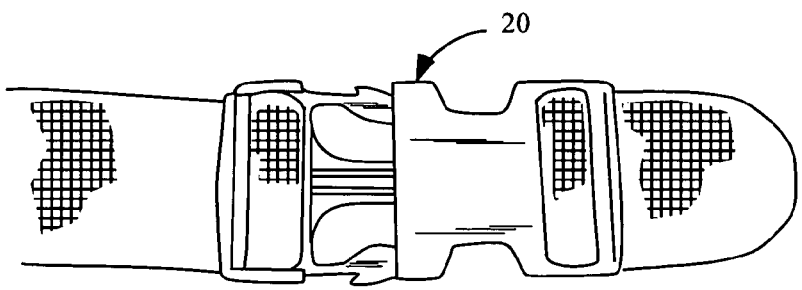
FIG. 6 is a drawing of a buckle for securing the waist band.

FIG. 6 is a buckle 20 for securing the single flap version of the waist band 4. The buckle 20 may be substituted for the right and left flaps of the second layer of the waist band 4.

Figure 7:
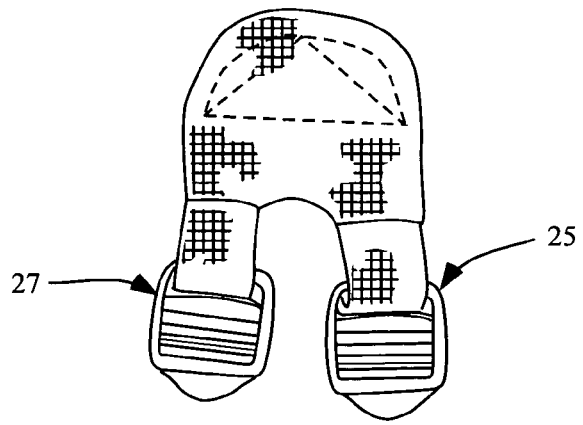
FIG. 7 is a drawing of another embodiment of the buckle for securing the waist band.

FIG. 7 is a dual buckle system 25, 27 for securing the second layer of the waist band which incorporates the right dual flaps 17, 19 and the left dual flaps 21, 23.

Figure 8:
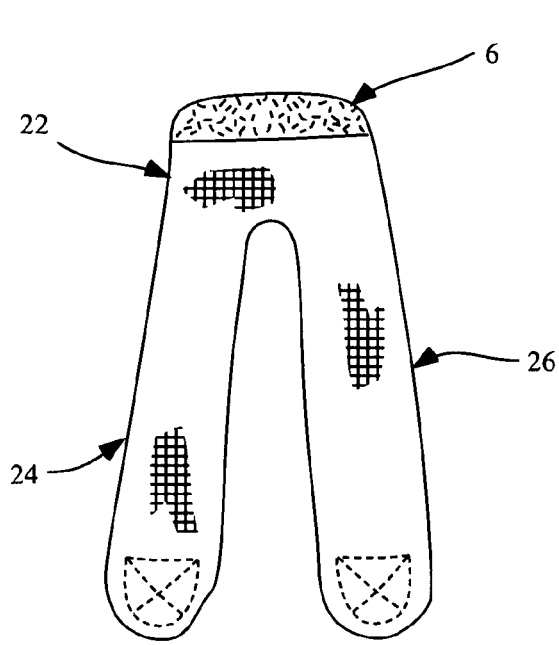
FIG. 8 is a drawing of the lateral vertical strap.

FIG. 8 is a drawing of the lateral vertical strap 6. The lateral vertical strap 6 is manufactured from an elastic material such as neoprene. In the present embodiment the lateral vertical strap 6 is manufactured from 4 mm neoprene. The lateral vertical strap 6 consists of a base 22, a first extension 24 and a second extension 26. The base 22 also consists of a hook and loop system that allows the base 22 to be secured to the waist band 4. On the first and second extensions 24, 26 opposite the base 22 also consists of a hook and loop system that allows the first and second extensions 24, 26 to be secured to the thigh band 10.

Figure 9:
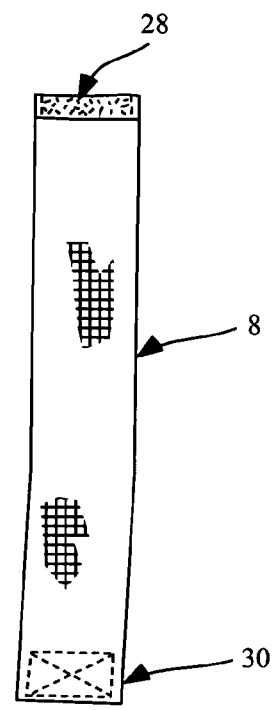
FIG. 9 is a drawing of the medial vertical strap.

FIG. 9 is a drawing of the medial vertical strap 8. The medial vertical strap 8 is manufactured from an elastic material. The medial vertical strap 8 consists of a first end 28 and a second end 30. Both the first end 28 and a second end 30 consists of a hook and loop system that allows the first end 28 to be secured to the waist band and the second end 30 to be secured to the thigh band.

Figure 10:
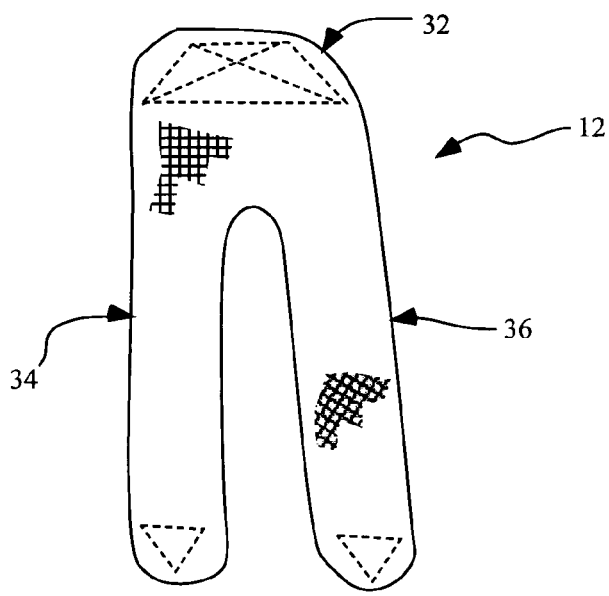
FIG. 10 is a drawing of the utility strap.

FIG. 10 is a drawing of the utility strap 12. The utility strap 12 is similar to the lateral vertical strap except smaller. In shorter people the utility strap 12 may be used as a replacement for the lateral vertical strap or it may be used in conjunction with the lateral vertical strap for added support. The utility strap 12 is manufactured from an elastic material such as neoprene. In the present embodiment the utility strap 12 is manufactured from 3 mm neoprene. The utility strap 12 consists of a base 32, a first extension 34 and a second extension 36. The base 32 also consists of a hook and loop system that allows the base 32 to be secured to the waist band. On the first and second extensions 34, 36 opposite the base 32 also consists of a hook and loop system that allows the first and second extensions 34, 36 to be secured to the thigh band.

Figure 11:
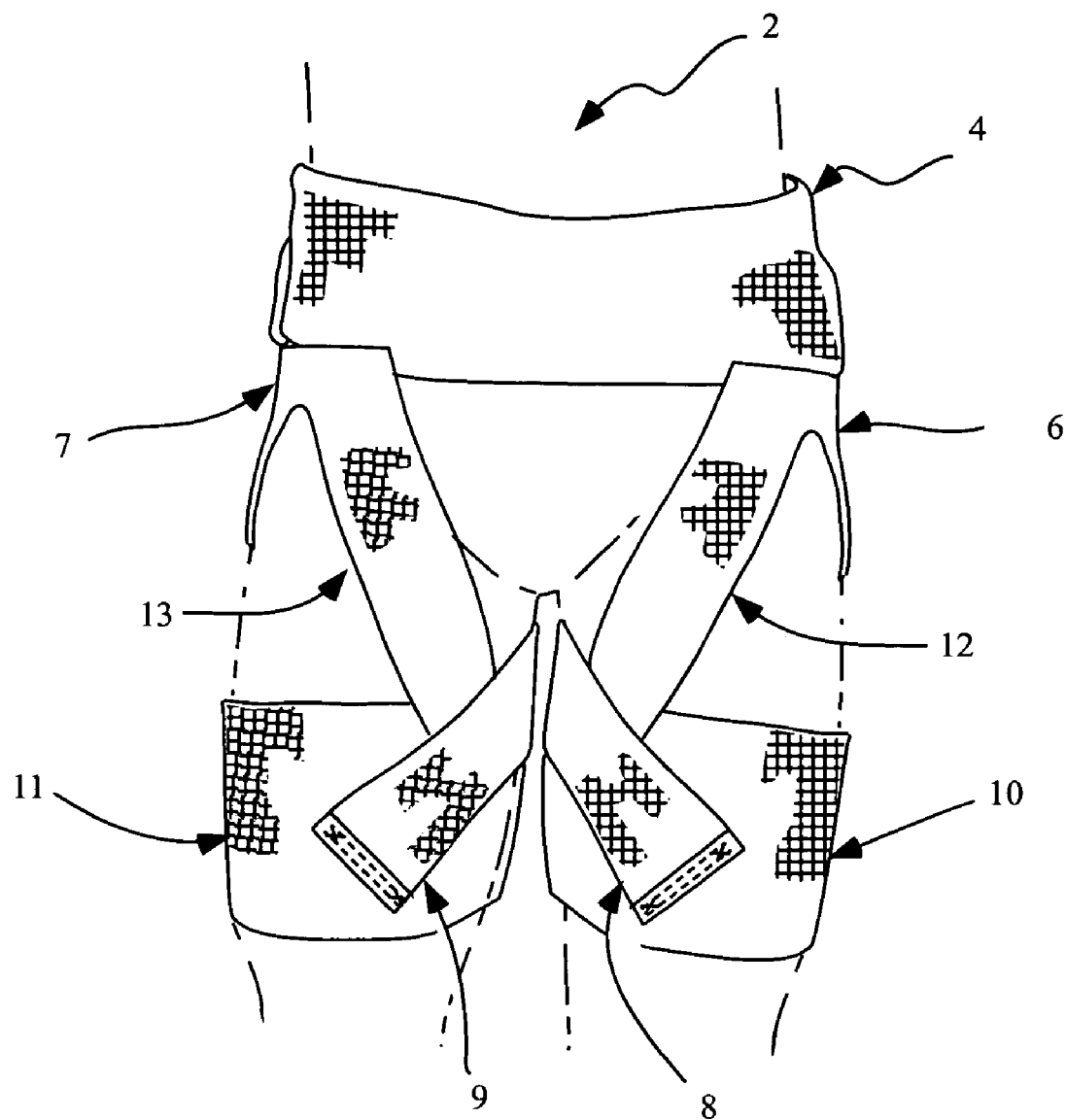
FIG. 11 is an anterior view of one embodiment of the hip brace as worn in a bilateral configuration.

FIG. 11 is an anterior view of one embodiment of the hip brace 2 as worn in a bilateral configuration. The hip brace 2 consists of a waist band 4, a first and second lateral vertical strap 6, 7, a first and second medial vertical strap 8, 9, and a first and second thigh band 10, 11. As seen in this view both the first and second lateral vertical strap 6, 7 are secured to the waist band 4 proximate to the side of the hip and a first extension 12, 13 is secured proximate the anterior aspect of the thigh band 10 between the lateral and medial aspect of the thigh band 10. Both of the medial vertical straps 8, 9 are secured to the posterior of the waist band 4 (not seen) then wraps down and around the leg and is secured to the thigh bands 10, 11 proximate the anterior aspect of said thigh band 10, 11 between the lateral and medial aspect of the thigh bands 10, 11.

While embodiments and applications of this disclosure have been shown and described, it would be apparent to those skilled in the art that many more modifications and improvements than mentioned above are possible without departing from the inventive concepts herein. The disclosure, therefore, is not to be restricted except in the spirit of the appended claims.

What is claimed is:

1. A support apparatus comprising:
    a waist band adapted to be wrapped around a person's waist;
    a thigh band adapted to be wrapped around one of said person's thigh proximate to said person's knee;
    a lateral vertical strap, having a first extension, second extension and a midpoint between said first and second extension, wherein said first extension of said lateral vertical strap is removeably attached to said thigh band proximate the anterior aspect of the thigh band between the medial aspect to lateral aspect of said thigh band, said midpoint of said lateral vertical strap is removeably attached to said waist band proximate the side of said person's hip, said second extension of said lateral vertical strap is attached to said thigh band proximate the posterior aspect of said thigh band between lateral and medial aspect of said thigh band; and
    a medial vertical strap, having a first and second end, wherein said first end of said medial vertical strap is removeably attached to said waist band proximate the rear of said person's hip descending medially along said thigh and wrapping around said thigh, said second end of said medial vertical strap is removeably attached to said thigh band proximate the anterior aspect of said thigh band between the lateral and medial aspect of said thigh band; and
    a utility band having a first end, a second end and a midpoint, wherein said first end of said utility band is removeably attached to said thigh band proximate the anterior aspect of the thigh band proximate the medial aspect of said thigh band, said midpoint of said utility band is removeably attached to said waist band proximate the front of said person's hip, said second end of said utility band is removeably attached to said thigh band proximate the anterior aspect of said thigh band proximate the lateral aspect of said thigh band.

2. The apparatus of claim 1 further comprising:
    a second thigh band adapted to be wrapped around said person's other thigh proximate to said person's knee;
    a second lateral vertical strap, having a first extension, second extension and a midpoint between said first and second extension, wherein said first extension of said lateral vertical strap is removeably attached to said second thigh band proximate the anterior aspect of the thigh band between the medial aspect to lateral aspect of said thigh band, said midpoint of said lateral vertical strap is removeably attached to said waist band proximate the side of said person's hip, said second extension of said lateral vertical strap is attached to said thigh band proximate the posterior aspect of said thigh band between said lateral and medial aspect of thigh band; and
    a second medial vertical strap, having a first and second end, wherein said first end of said medial vertical strap is removeably attached to said waist band proximate the rear of said person's hip descending medially along said thigh and wrapping around said thigh, said second end of said medial vertical strap is removeably attached to said thigh band proximate the anterior aspect of said thigh band between the lateral and medial aspect of said thigh band.

3. The apparatus of claim 2 further comprising:
    a second utility band having a first end, a second end and a midpoint, wherein said first end of said utility band is removeably attached to said second thigh band proximate the anterior aspect of the thigh band proximate the medial aspect said thigh band, said midpoint of said second utility band is removeably attached to said waist band proximate the front of said person's hip, said second end of said second utility band is removeably attached to said thigh band proximate the anterior aspect of said second thigh band proximate the lateral aspect of said thigh band.

4. The apparatus of claim 3 wherein said waist band further comprises:
- a first layer having an interior and exterior, said exterior having a hook and loop system;
- a second layer having a right flap and a left flap, said right flap and left flap attached to the first layer at a point proximate to a midpoint of said first layer.

5. The apparatus of claim 4 wherein said waistband further comprises:
- a first end and a second end, said first end removeably fastened to said second end.

6. The apparatus of claim 5 further comprising:
- a hook and loop system to fasten said first end and said second end of said waist band and said right and left flap.

7. The apparatus of claim 6 further comprising:
- a buckle system to fasten said first end and said second end of said waist band and said right flap and said left flap.

8. The apparatus of claim 7 wherein said waist band is manufactured from neoprene.

9. The apparatus of claim 8 wherein said neoprene is 2-3 mm thick.

10. A method for supporting a person's hip comprising:
providing a waist band;
wrapping said waist band around a person's waist;
providing a thigh band;
wrapping said thigh band around said person's thigh proximate to said person's knee;
providing a lateral vertical strap, having a first end, second end and a midpoint between said first and second end;
attaching said first end of said lateral vertical strap to said thigh band proximate the anterior aspect of the thigh band between the medial aspect to lateral aspect of said thigh band;
attaching said midpoint of said lateral vertical strap to said waist band proximate the side of said person's hip;
attaching said second end of said lateral vertical strap to said thigh band proximate the posterior aspect of said thigh band between lateral and medial aspect of thigh band;
providing a medial vertical strap, having a first and second end;
attaching said first end of said medial vertical strap to said waist band proximate the rear of said person's hip; and
attaching said second end of said medial vertical strap to said thigh band proximate the anterior aspect of said thigh band between the lateral and medial aspect of said thigh band.

11. The method of claim 10 further comprising:
providing a utility band having a first end, a second end and a midpoint;
attaching said first end of said utility band to said thigh band proximate the anterior aspect of the thigh band proximate the medial aspect said thigh band;
attaching said midpoint of said utility band to said waist band proximate the front of said person's hip; and
attaching said second end of said utility band to said thigh band proximate the anterior aspect of said thigh band proximate the lateral aspect of said thigh band.

12. The method of claim 11 further comprising:
providing a second thigh band;
wrapping said second thigh band around said person's other thigh proximate to said person's knee;
providing a second lateral vertical strap, having a first end, second end and a midpoint between said first and second end;
attaching said first end of said second lateral vertical strap to said second thigh band proximate the anterior aspect of said second thigh band between the medial aspect to lateral aspect of said second thigh band;
attaching said midpoint of said second lateral vertical strap to said waist band proximate the side of said person's hip;
attaching said second end of said second lateral vertical strap to said second thigh band proximate the posterior aspect of said thigh band between lateral and medial aspect of said second thigh band;
providing a second medial vertical strap, having a first and second end;
attaching said first end of said second medial vertical strap to said waist band proximate the rear of said person's hip; and
attaching said second end of said second medial vertical strap to said second thigh band proximate the anterior aspect of said second thigh band between the lateral and medial aspect of said second thigh band.

13. The method of claim 12 further comprising:
providing a second utility band having a first end, a second end and a midpoint;
attaching said first end of said second utility band to said second thigh band proximate the anterior aspect of said second thigh band proximate the medial aspect of said second thigh band;
attaching said midpoint of said second utility band to said waist band proximate the front of said person's hip; and
attaching said second end of said second utility band to said second thigh band proximate the anterior aspect of said second thigh band proximate the lateral aspect of said second thigh band.

* * * * *